US012576203B2

(12) United States Patent
Dick, Jr.

(10) Patent No.: US 12,576,203 B2
(45) Date of Patent: Mar. 17, 2026

(54) FLUID COLLECTION CANISTER FOR USE WITH SUB-ATMOSPHERIC PRESSURE PUMP

(71) Applicant: Renovo Concepts, Inc., San Antonio, TX (US)

(72) Inventor: Larry Daniel Dick, Jr., San Antonio, TX (US)

(73) Assignee: Renovo Concepts, Inc., San Antonio, TX (US)

( * ) Notice: Subject to any disclaimer, the term of this patent is extended or adjusted under 35 U.S.C. 154(b) by 0 days.

(21) Appl. No.: 18/425,160

(22) Filed: Jan. 29, 2024

(65) Prior Publication Data

US 2024/0424184 A1      Dec. 26, 2024

Related U.S. Application Data

(60) Provisional application No. 63/441,830, filed on Jan. 29, 2023.

(51) Int. Cl.
A61M 1/00          (2006.01)
B65D 6/24          (2006.01)
(52) U.S. Cl.
CPC ............. A61M 1/60 (2021.05); B65D 11/188 (2013.01)
(58) Field of Classification Search
CPC ......... B65D 11/188; A61M 1/63; A61M 1/60; B60K 15/03006; B60K 15/03
USPC ........ 220/86.1, 4.14, 4.12, 4.24; 141/46, 18, 141/375
See application file for complete search history.

(56) References Cited

U.S. PATENT DOCUMENTS

| | | | | |
|---|---|---|---|---|
| 4,655,754 A | * | 4/1987 | Richmond | .............. A61M 1/60 604/323 |
| 6,138,859 A | * | 10/2000 | Aulph | .................... B60K 15/03 137/574 |
| 6,293,419 B1 | * | 9/2001 | Farrar | .................. F02M 37/103 220/23.89 |
| 2007/0272696 A1 | * | 11/2007 | Kallevig | ................ B60K 15/04 220/562 |
| 2009/0240218 A1 | * | 9/2009 | Braga | ................... A61M 1/984 604/313 |
| 2011/0220644 A1 | * | 9/2011 | Yager | ..................... B60K 15/04 220/86.1 |

(Continued)

FOREIGN PATENT DOCUMENTS

| | | | | | |
|---|---|---|---|---|---|
| CA | 2443247 A1 | * | 1/1995 | .......... | A61M 1/0001 |
| WO | WO-9601226 A1 | * | 1/1996 | ............. | B65D 85/84 |

*Primary Examiner* — Robert J Hicks
(74) *Attorney, Agent, or Firm* — Kammer Browning PLLC; Mark A. Kammer

(57)          ABSTRACT

A fluid separation and collection canister operable in-line between a sub-atmospheric pump and a source of mixed fluid-gas flow. In one application, the present invention finds particular use in a healthcare environment to assist in the removal of fluids from a patient with internal or external injuries. The enclosed collection canister is made up of two case half shells separable at mid-line overlapping joint. The upper case half shell incorporates a suction port with a sub-micron gas filter, a pass-through port, and an upper fluid extraction port. The lower case half shell incorporates an inlet port with a one-way fluid valve, a lower pass-through port, and a lower fluid extraction port. The pass-through ports are used to carry a pressure monitoring lumen to the source of the mixed fluid-gas flow.

12 Claims, 9 Drawing Sheets

(56)                    References Cited

U.S. PATENT DOCUMENTS

2019/0263216 A1*   8/2019  Fellague ............ B60G 21/0556
2023/0313493 A1*  10/2023  Hirose ................. E02F 9/0883
                                                      220/563

* cited by examiner

FLUID COLLECTION CANISTER FOR USE WITH SUB-ATMOSPHERIC PRESSURE PUMP

CROSS REFERENCES TO RELATED APPLICATIONS

This Application claims the benefit under Title 35 United States Code § 119 (e) of U.S. Provisional Patent Application Ser. No. 63/441,830; Filed: Jan. 29, 2023, the full disclosure of which is incorporated herein by reference.

BACKGROUND OF THE INVENTION

1. Field of the Invention

The present invention relates generally to systems for separating and containing fluids from a mixed fluid-gas flow. The present invention relates more specifically to a fluid separation and collection canister operable in-line between a sub-atmospheric pump and a source of mixed fluid-gas flow. In one application, the present invention is used in a health-care environment to assist in the removal of fluids from a patient for purposes of healing internal and external wounds.

2. Description of the Related Art

There are many systems and environments associated with industrial and medical processes where it is necessary or beneficial to draw from a source of mixed fluid-gas flow and to separate the flow into the fluid and gas constituents. It is further beneficial to thereafter contain the separated fluid constituents for later analysis and/or disposal, and to vent or disperse the gas constituents in a controlled and safe manner.

The typical aspiration canister found in association with medical procedures and healthcare environments provides a sealed container (often clear sided for monitoring a level of collected fluids) with a suction port connected to a suction pump and an inlet port connected to the mixed fluid-gas flow source. The suction port typically opens into the container at a point near the top of the container while the inlet port opens into the container at a lower point where fluids may flow (by force of gravity) into a lower portion of the canister. Such aspiration canisters serve adequately where flow rates are significant, and monitoring of the suction forces is not critical. At lower flow rates and under conditions where the sub-atmospheric pressures (suction) must be more carefully maintained and monitored, the existing devices in the field often fail to achieve the safety and efficiency required.

SUMMARY OF THE INVENTION

The present invention is intended to be used in a wide range of systems that require or benefit from the removal and containment of fluids from a mixed fluid-gas flow stream. An exemplary application of the present invention may be used in some instances with the Mechanical Tissue Resuscitation Systems and Methods generally described in U.S. Pat. No. 8,267,960, Issued: Sep. 18, 2012, Title: Device and Method for Treating Central Nervous System Pathology; and in U.S. Pat. No. 8,764,794, Issued: Jul. 1, 2014, Title: Device and Method for Treating Central Nervous System Pathology; the full disclosures of which are each incorporated herein by reference. While the present invention finds particular application to the requirements of the above described systems and methods, the basic structures and functions of the devices of the present invention are broadly applicable to a range of industrial and medical environments.

The present invention provides a fluid separation and collection canister operable in-line between a sub-atmospheric pump and a source of mixed fluid-gas flow. In one application, the present invention finds particular use in a healthcare environment to assist in the removal of fluids from a patient with internal or external injuries. In a specific healthcare environment, the present invention facilitates the functionality of mechanical tissue resuscitation systems and methods such as may be utilized in connection with traumatic injuries to the central nervous system.

The present invention provides an enclosed collection canister made up of two case half shells separable at mid-line overlapping joint. The upper case half shell incorporates a suction port with a sub-micron gas filter, a pass-through port, and an upper fluid extraction port. The lower case half shell incorporates an inlet port with a one-way fluid valve, a lower pass-through port, and a lower fluid extraction port.

BRIEF DESCRIPTION OF THE DRAWING FIGURES

FIGS. 4A-4C are perspective views of the upper portion (FIG. 4A) and the lower portion (FIGS. 4B & 4C) of the fluid collection canister of the present invention, showing the external configuration of the canister halves as well as the internal flow and containment configuration of the canister halves.

DESCRIPTION OF THE EXEMPLARY EMBODIMENTS

Figure 1:
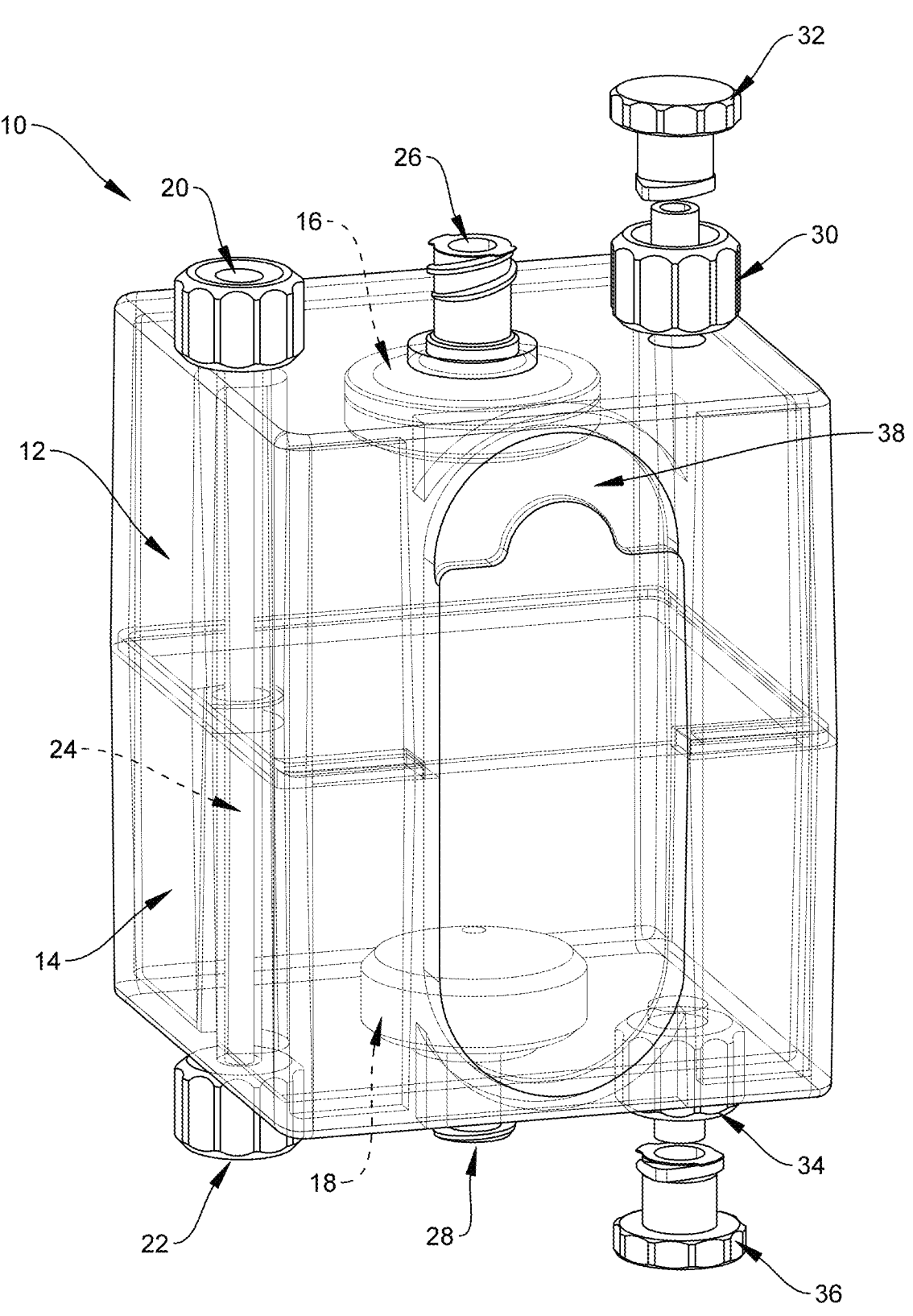
FIG. 1 is a perspective view of the fluid collection canister of the present invention, showing the external configuration of the canister as well as the internal flow and containment configuration of the canister (as seen through the transparent walls of the enclosure).

FIG. 1 is a perspective view of the fluid collection canister of the present invention, showing the external configuration of the canister as well as the internal flow and containment configuration of the canister (as seen through the transparent walls of the enclosure). The present invention provides an enclosed collection canister 10 made up of two case half shells 12 & 14 separable at mid-line overlapping joint. The upper case half shell 12 incorporates a suction port 26 with a sub-micron gas filter 16, a pass-through port 20, and an upper fluid extraction port 30 with luer port cap 32. The upper case half shell 12 incorporates canister mounting bracket 38 on the exterior of the case. The lower case half shell 14 incorporates an inlet port 28 with a one-way fluid valve 18, a lower pass-through port 22, and a lower fluid extraction port 34 with luer cap 36.

In operation, primary outlet (suction) port 26 connects to a sub-atmospheric pressure pump (not shown) thereby drawing a suction through the canister. Fluid is prevented from exiting the canister through the outlet port by way of sub-micron gas filter 16. The mixed fluid-gas flow is drawn into the canister through inlet port 28. The flow is prevented from reversing back out port 28 by way of one-way valve 18. Although the generally vertical orientation of the canister established by hanging the device on a support (not shown) with canister mounting bracket 38 serves to maintain collected fluids in the lower portion of the canister by gravitational separation, such vertical orientation is not critical because of sub-micron gas filter 16 and one-way valve 18.

The pass-through feature of the canister shown in FIG. 1 accommodates a dual-transducer monitoring capability in the above described sub-atmospheric pressure pump system. This capability requires one applied suction pathway (through the main body of the canister) and one reference pathway (through an isolated section of the canister). Pressure at the source site may be monitored by way of a closed lumen extending from the source through lower pass-through port 22, pass-through tube 24 (within but isolated from the canister enclosure), and finally through upper pass-through port 20. Upper pass-through port 20 may be connected to an operational pressure monitor typically associated with the sub-atmospheric pressure pump. Tubular connections to and from the canister may be separate single lumen conduits or single, multi-lumen conduits.

Fluid (and gas, if appropriate) may be extracted from collection canister 10 during or after operation of the system by connection to either or both of upper and lower fluid extraction ports 30 & 34. When not in use, extraction ports 30 & 34 may be closed with luer port caps 32 & 36 as shown in the figures. Although the size of the canister may vary, medical applications such as those discussed above may preferably use a container capable of holding 100 milliliters.

Figure 2:
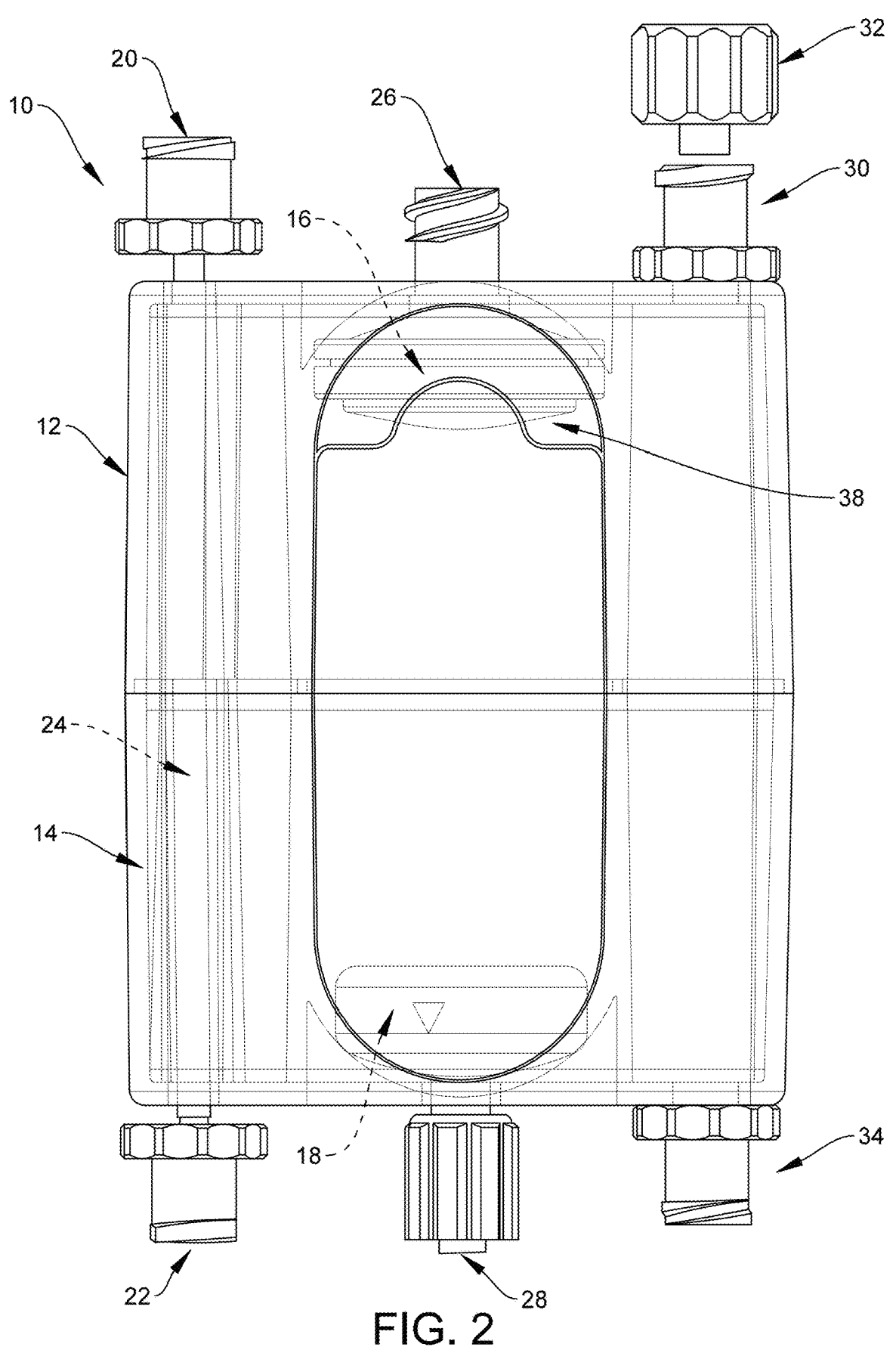
FIG. 2 is a front elevational view of the fluid collection canister of the present invention, showing the external configuration of the canister as well as the internal flow and containment configuration of the canister (as seen through the transparent walls of the enclosure).

FIG. 2 is a front elevational view of the fluid collection canister of the present invention, showing the external configuration of the canister as well as the internal flow and containment configuration of the canister (as seen through the transparent walls of the enclosure). The components of canister 10 shown in FIG. 2 are the same or similar to the corresponding components described above in FIG. 1.

Figure 3A:
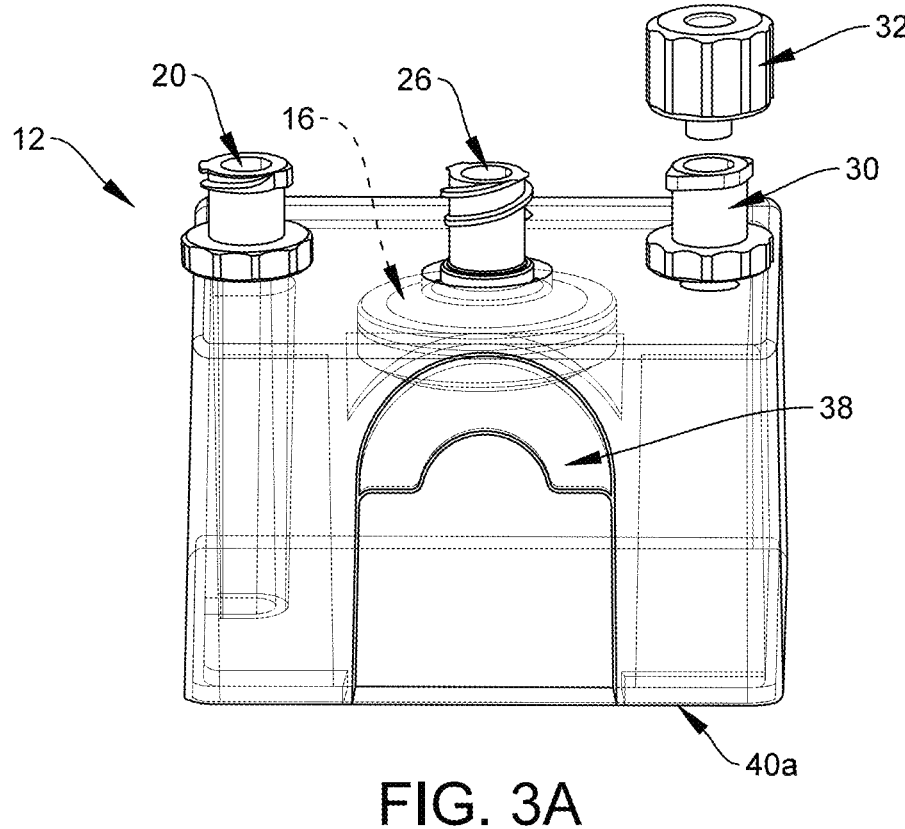
FIGS. 3A & 3B are front elevational views of the upper portion (FIG. 3A) and the lower portion (FIG. 3B) of the fluid collection canister of the present invention, showing the external configuration of the canister halves as well as the internal flow and containment configuration of the canister halves.
Figure 3B:
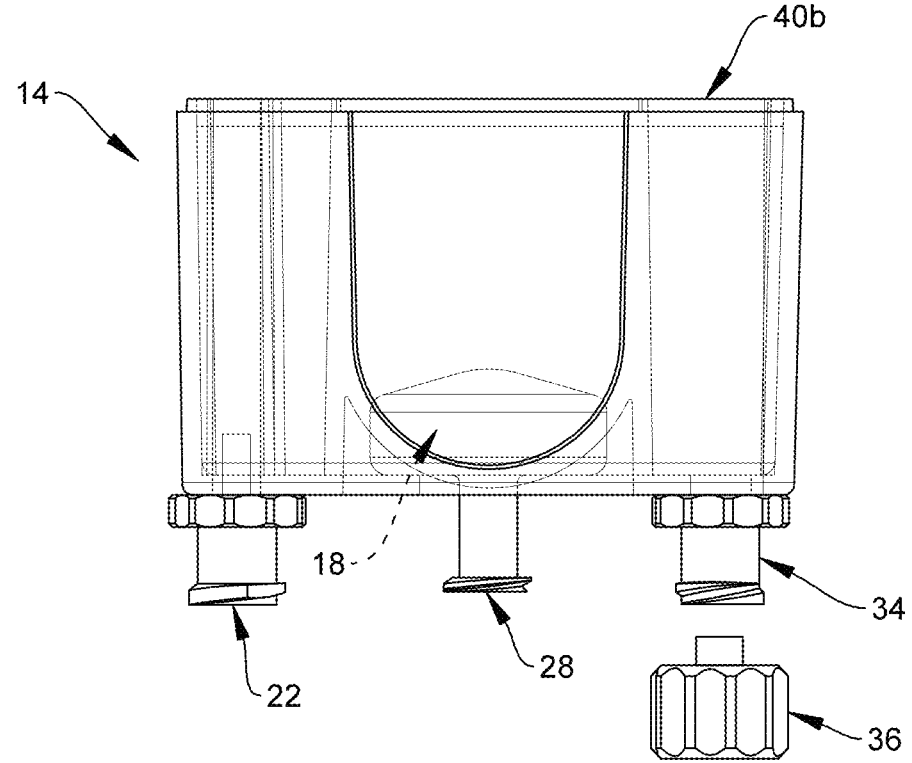

FIGS. 3A & 3B are front elevational views of the upper portion (FIG. 3A) and the lower portion (FIG. 3B) of the fluid collection canister of the present invention, showing the external configuration of the canister halves as well as the internal flow and containment configuration of the canister halves. Shown in FIGS. 3A & 3B are upper overlapping joint 40a (FIG. 3A) and lower overlapping joint 40b (FIG. 3B). This overlapping joint may be a separable press-fit connection between the case half shells or may be a more permanent joint sealed with an appropriate adhesive. The components of the canister shown in FIGS. 3A & 3B are the same or similar to the corresponding components described above in FIG. 1.

Figures 4A, 4B, 4C:
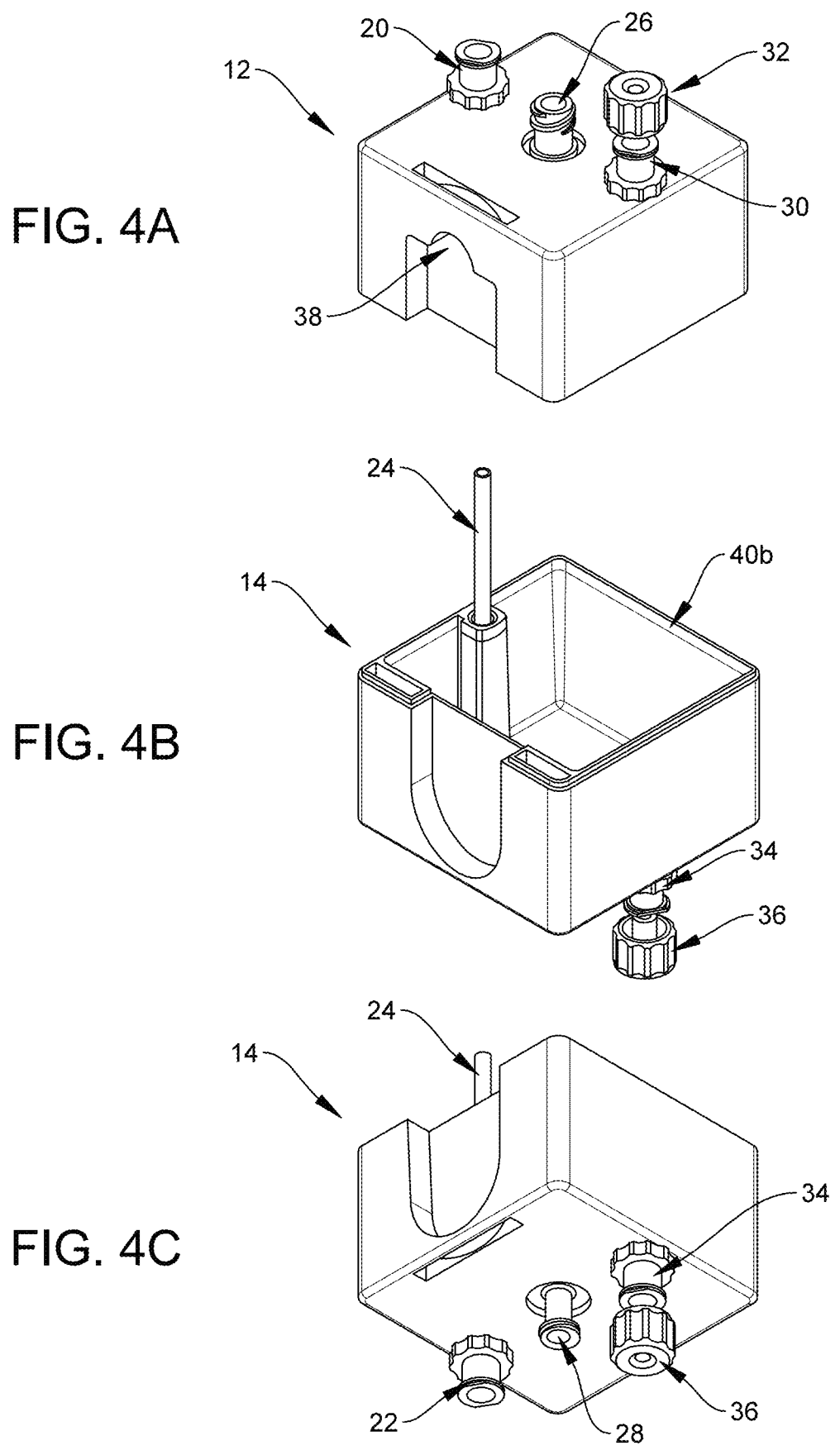

FIGS. 4A-4C are perspective views of the upper portion (FIG. 4A) and the lower portion (FIGS. 4B & 4C) of the fluid collection canister of the present invention, showing the external configuration of the canister halves as well as the internal flow and containment configuration of the canister halves. The components of the canister shown in FIGS. 4A-4C are the same or similar to the corresponding components described above in FIG. 1.

Although the entire canister is preferably constructed from a transparent material (such as clear acrylic plastic) that allows for visual inspection of the contents, a "sight glass" walled portion of each of the case half shells may be structured with volumetric gradations for visual reference. Use of the canister mounting bracket may be facilitated by structuring an oblong guide slot immediately below the mounting bracket 38 on the "back side" of the rectangular enclosure.

Figure 5A:
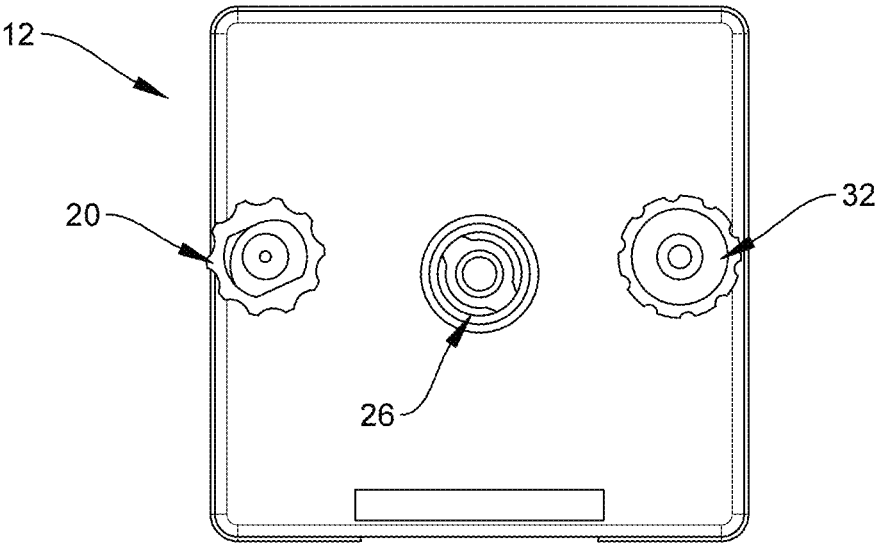
FIGS. 5A & 5B are top plan (FIG. 5A) and front elevational (FIG. 5B) views of the upper portion of the fluid collection canister of the present invention, showing the external configuration of the upper portion of the canister.
Figure 5B:
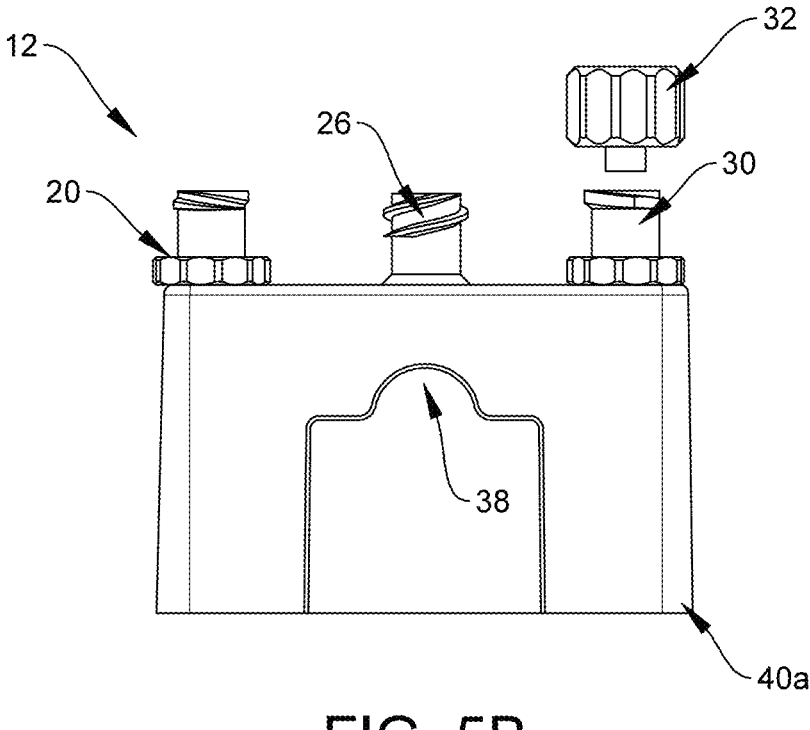

FIGS. 5A & 5B are top plan (FIG. 5A) and front elevational (FIG. 5B) views of the upper portion of the fluid collection canister of the present invention, showing the external configuration of the upper portion of the canister. Once again, the components of the canister shown in FIGS. 5A & 5B are the same or similar to the corresponding components described above in FIG. 1.

Figure 6A:
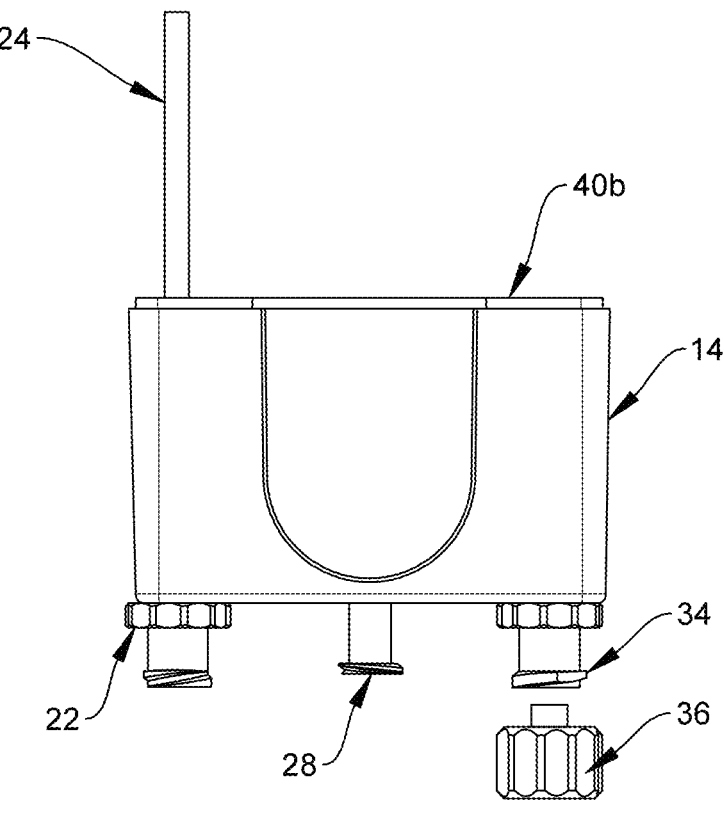
FIGS. 6A & 6B are front elevational (FIG. 6A) and bottom plan (FIG. 6B) views of the lower portion of the fluid collection canister of the present invention, showing the external configuration of the lower portion of the canister.
Figure 6B:
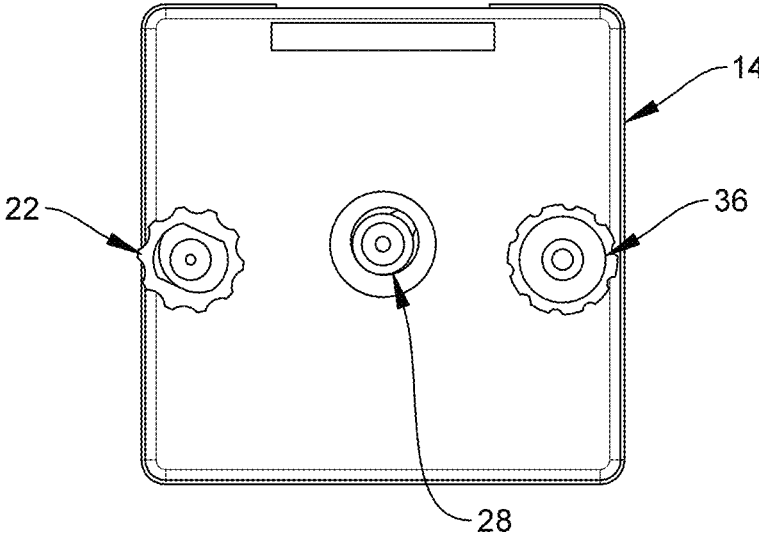
Figures 7A, 7B:
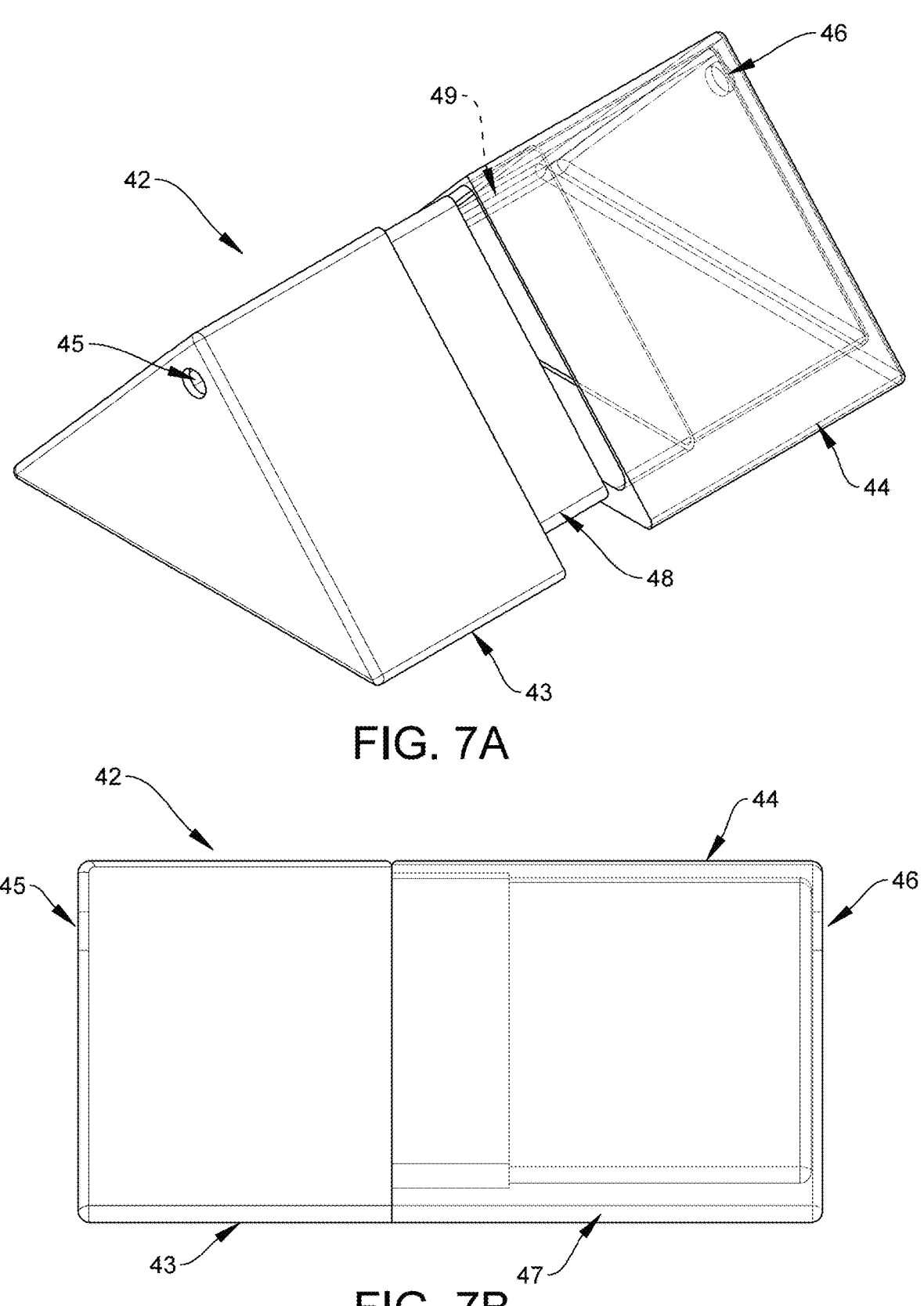
FIGS. 7A & 7B are perspective (FIG. 7A) and side plan (FIG. 7B) views of an alternate embodiment of the present invention structured as a two-part triangular prism enclosure with inlet and outlet ports positioned at the peaks of the triangular end walls.

FIGS. 6A & 6B are front elevational (FIG. 6A) and bottom plan (FIG. 6B) views of the lower portion of the fluid collection canister of the present invention, showing the external configuration of the lower portion of the canister. Once again, the components of the canister shown in FIGS. 6A & 6B are the same or similar to the corresponding components described above in FIG. 1. Alternate embodiments of the present invention are disclosed in FIGS. 7A & 7B and FIGS. 8A & 8B. FIGS. 7A & 7B are perspective (FIG. 7A) and side plan (FIG. 7B) views of an alternate embodiment of the present invention structured as a two-part triangular prism enclosure 42 with first case side shell 43 and second case side shell 44. The case side shells 43 & 44 connect at mid-line overlapping joint sections 48 & 49. Inlet and outlet ports 45 & 46 are positioned at the peaks of the triangular end walls. One objective of the embodiment shown in FIGS. 7A & 7B is to provide a stable base to maintain the orientation of the canister without the need for a hanging bracket. The base wall 47 of the device is preferably thicker than the side walls, again to facilitate the stability of the canister.

Figure 8A:
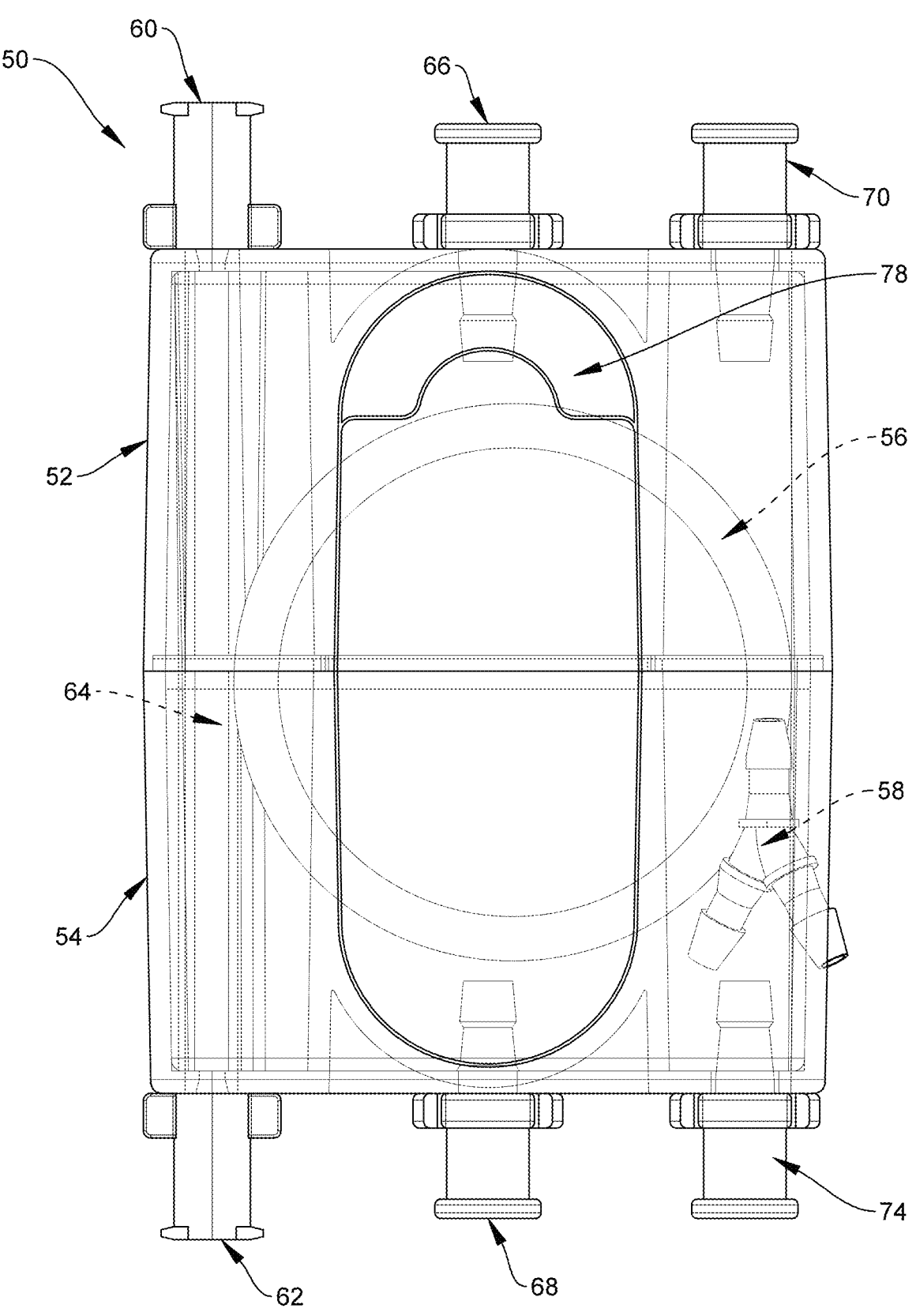
FIGS. 8A & 8B are front elevational (FIG. 8A) and exploded perspective (FIG. 8B) views of an alternate embodiment of the present invention, essentially as described in association with FIGS. 1 & 2 but with an internal fluid distribution coil that facilitates the separation and collection of the fluid.
Figure 8B:
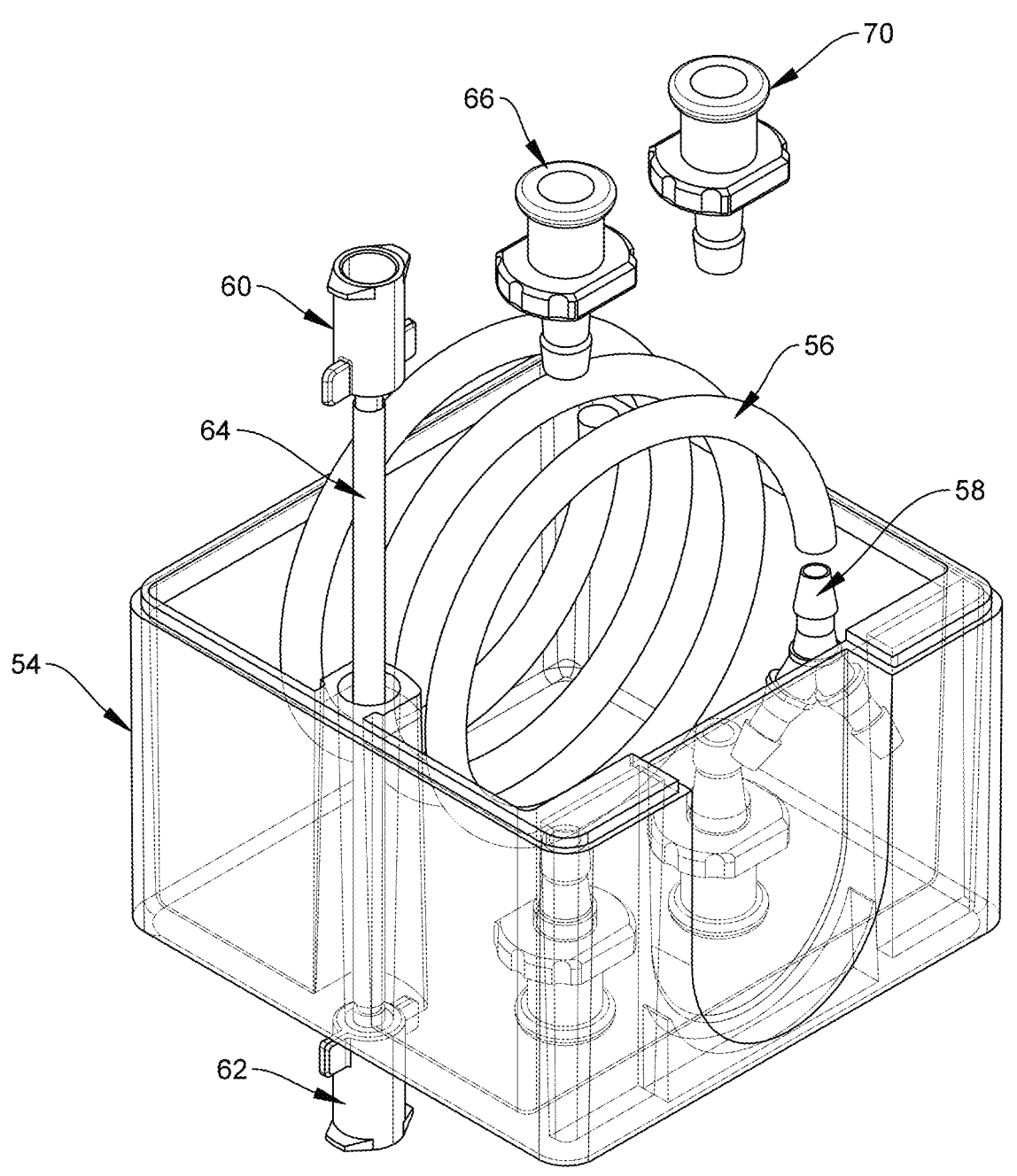

FIGS. 8A & 8B are front elevational (FIG. 8A) and exploded perspective (FIG. 8B) views of an alternate embodiment of the present invention, essentially as described in association with FIGS. 1 & 2 but with an internal fluid distribution coil that facilitates the separation and collection of the fluid, especially where the lower portion of the enclosure might include a volume of retention foam or a quantity of solidifying agent. FIG. 8A is a front elevational view of this alternate embodiment of the fluid collection canister of the present invention, showing the external configuration of the canister as well as the internal flow and containment configuration of the canister (as seen through the transparent walls of the enclosure). This alternate embodiment provides an enclosed collection canister 50 made up of two case half shells 52 & 54 separable at mid-line overlapping joint. The upper case half shell 52 incorporates a suction port 66 on which a sub-micron gas filter (not shown) may be fixed, a pass-through port 60, and an upper fluid extraction port 70. The upper case half shell 52 incorporates canister mounting bracket 78 on the exterior of the case. The lower case half shell 54 incorporates an inlet port 68 on which a one-way fluid valve (not shown) may be fixed, a lower pass-through port 62, and a lower fluid extraction port 74.

In operation, primary outlet (suction) port 66 of the canister of the alternate embodiment shown FIGS. 8A & 8B connects to a sub-atmospheric pressure pump (not shown) thereby drawing a suction through the canister. The mixed fluid-gas flow is drawn into the canister through inlet port 68. In this alternate embodiment, the flow is drawn from inlet port 68 through a connected tubing coil 56 to a distribution "Y" outlet 58. The tubing coil 56 and the "Y" outlet 58 are shown separated from each other and from inlet port 68 in FIGS. 8A & 8B as they may be oriented within the enclosure to distribute the flow into either the upper case half shell 52 of the canister or the lower case half shell 54. A preferred orientation may depend on whether the lower portion of the enclosure might include a volume of retention foam or a quantity of solidifying agent.

As with the embodiment shown in FIGS. 1 & 2, the generally vertical orientation of the canister established by hanging the device on a support (not shown) with canister mounting bracket 78 serves to maintain collected fluids in the lower portion of the canister by gravitational separation. However, such vertical orientation is not essential where a sub-micron gas filter (not shown) and a one-way valve (not shown) are utilized.

Also, as with the embodiment shown in FIGS. 1 & 2, the pass-through feature of the canister shown in FIGS. 8A & 8B accommodates a dual-transducer monitoring capability in the above described sub-atmospheric pressure pump system. This capability requires one applied suction pathway (through the main body of the canister) and one reference pathway (through an isolated section of the canister). Pressure at the source site may be monitored by way of a closed lumen extending from the source through lower pass-through port 62, pass-through tube 44 (within but isolated from the canister enclosure), and finally through upper pass-through port 60. Upper pass-through port 60 may be connected to an operational pressure monitor typically associated with the sub-atmospheric pressure pump. Tubular connections to and from the canister may be separate single lumen conduits or single, multi-lumen conduits.

Finally in the embodiment of FIGS. 8A & 8B, fluid (and gas, if appropriate) may be extracted from collection canister 50 during or after operation of the system by connection to either or both of upper and lower fluid extraction ports 70 & 74. When not in use, extraction ports 70 & 74 may be closed with luer port caps (not shown). Once again, although the size of the alternate embodiment canister may vary, medical applications such as those discussed above may preferably use a container capable of holding 100 milliliters.

Although the present invention has been described in association with a specific medical application, those skilled in the art will recognize additional fields of application both within and outside of healthcare environments. Many industrial systems utilize or encounter a flow of a mixture of fluids and gases that benefit from a process step involving the separation of the fluids from the gaseous flow. The present invention finds applicability wherever pneumatic and hydraulic flow systems interact and it proves beneficial to later extract or separate the fluids from the flow stream. The device of the present invention finds specific application in medicine where sub-atmospheric pressures are utilized for the aspiration or extraction of fluids from a patient's body or from specific tissue.

In some applications it may be preferable to utilize a volume of fluid retention foam within a portion of the space within the container. In other applications it may be preferable to pre-fill a portion of the container with a solidifying compound or a gelling compound to mix with the collected fluids. In each instance, the purpose is to help retain the collected fluid in a single mass in the lower portion of the canister and to physically stabilize the collected fluid.

I claim:

1. A fluid separation and collection canister operable in-line between a sub-atmospheric pump and a source of mixed fluid-gas flow, the collection canister comprising:
   an upper case half shell comprising:
      a suction port with a sub-micron gas filter;
      an upper pass-through port; and
      an upper fluid extraction port;
   a lower case half shell attached to and separable from the upper case half shell at a mid-line overlapping joint, the lower case half shell comprising:
      an inlet port with a one-way fluid valve;
      a lower pass-through port; and
      a lower fluid extraction port;
   wherein attachment of the lower case half shell to the upper case half shell at the mid-line overlapping joint defines a sealed canister enclosure flow accessible through the suction port, the inlet port, the pass-through ports, and the fluid extraction ports.

2. The fluid separation and collection canister of claim 1 further comprising a pass-through conduit extending from the lower pass-through port to the upper pass-through port.

3. The fluid separation and collection canister of claim 1 wherein the upper fluid extraction port further comprises a removable luer cap.

4. The fluid separation and collection canister of claim 1 wherein the lower fluid extraction port further comprises a removable luer cap.

5. The fluid separation and collection canister of claim 1 wherein the upper case half shell further comprises a canister mounting bracket, the mounting bracket facilitating hanging of the canister in a generally vertical orientation.

6. The fluid separation and collection canister of claim 1 wherein at least a portion of the upper case half shell, and a portion of the lower case half shell, comprise generally transparent walls, wherein any fluid contents within the canister are externally visible.

7. The fluid separation and collection canister of claim 1 further comprising an internal fluid distribution coil in flow connection with the inlet port, the internal fluid distribution coil opening into the interior of the canister.

8. The fluid separation and collection canister of claim 7 wherein the internal fluid distribution coil is oriented to open into an interior of the upper case half shell.

9. The fluid separation and collection canister of claim 7 wherein the internal fluid distribution coil is oriented to open into an interior of the lower case half shell.

10. The fluid separation and collection canister of claim 7 wherein the internal fluid distribution coil terminates with a multi-port opening, wherein the multi-port opening facilitates a wider distribution of fluids flowing into the canister.

11. A fluid separation and collection system for connection to a source of mixed fluid-gas flow, the system comprising:
   a sub-atmospheric pump;

a collection canister connected in-line between the sub-atmospheric pump and the source of mixed fluid-gas flow, the collection canister comprising:

a shell enclosure having: a suction port and an inlet port; upper and lower pass-through ports connecting a segregated pass-through conduit; and upper and lower fluid-gas extraction ports;

a first pressure transducer for monitoring pressure in an applied suction pathway through the collection canister, the first pressure transducer in flow communication with the suction port; and a second pressure transducer for monitoring pressure in a reference pathway in the segregated pass-through conduit, the second pressure transducer in flow communication with upper pass-through port;

wherein the system simultaneously monitors pressures within the canister and at the source of mixed fluid-gas flow.

12. The fluid separation and collection system of claim 11 wherein the sub-atmospheric pump and the first and second pressure transducers are connected to the canister through a first dual-lumen conduit, and the canister is connected to the source of mixed fluid-gas flow through a second dual-lumen conduit.

* * * * *